United States Patent [19]

Fischer et al.

[11] 4,137,326

[45] Jan. 30, 1979

[54] USE OF MAGNESIUM MONOSPARTATE HYDROCHLORIDE COMPLEX

[75] Inventors: Franz Fischer; Joachim Helbig, both of Tutzing, Fed. Rep. of Germany

[73] Assignee: Verla-Pharm Arzneimittelfabrik, Apotheker H.J.V. Ehrlich, Munich, Fed. Rep. of Germany

[21] Appl. No.: 771,421

[22] Filed: Feb. 24, 1977

Related U.S. Application Data

[63] Continuation-in-part of Ser. No. 567,366, Apr. 11, 1975, abandoned, which is a continuation-in-part of Ser. No. 105,731, Jan. 11, 1971, abandoned.

[51] Int. Cl.$^2$ ............................................. A61K 31/195
[52] U.S. Cl. ....................................... 424/319; 562/571

[58] Field of Search ...................... 424/319; 260/534 E

[56] References Cited

U.S. PATENT DOCUMENTS

3,836,668  9/1974  Battles et al. ........................ 424/319

OTHER PUBLICATIONS

Chemical Abstracts 53:3477a (1959).
Chemical Abstracts 57:14367g (1962).

*Primary Examiner*—Jerome D. Goldberg
*Attorney, Agent, or Firm*—Connolly and Hutz

[57] ABSTRACT

The invention disclosed concerns a magnesium monospartate hydrochloride and more particularly its use in the prophylaxis of heart necroses.

6 Claims, No Drawings

USE OF MAGNESIUM MONOSPARTATE HYDROCHLORIDE COMPLEX

This is a continuation-in-part of copending application Ser. No. 567,366 filed Apr. 11, 1975, now abandoned which is in turn a continuation-in-part of application Ser. No. 105,731 filed Jan. 11, 1971, now abandoned. The invention relates to a method of using a magnesium monospartate hydrochloride complex.

The magnesium monospartate complex employed in the present invention is of the formula:

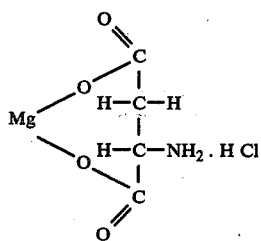

The magnesium monospartate hydrochloride is prepared from magnesium diaspartate by the addition of hydrogen chloride. The reaction proceeds according to the following reaction scheme.

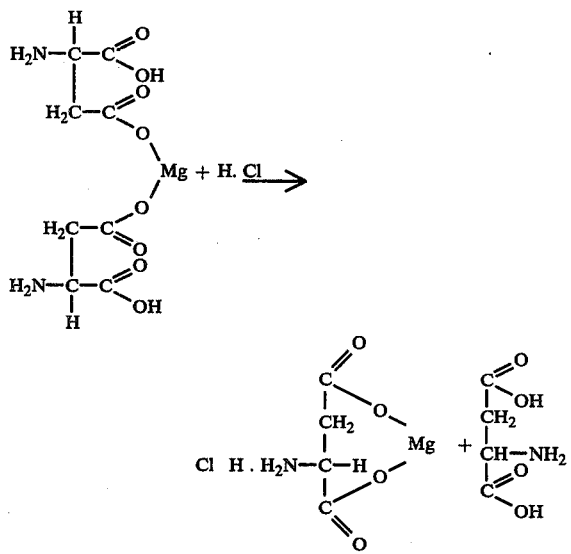

The reaction is carried out most suitably in an aqueous medium using stoichiometric amounts of the reactants. The precipitated aspartic acid is filtered off after completion of the reaction. After concentrating the filtrate, the magnesium monospartate hydrochloride is crystallized out or most preferably obtained by spray drying. The compound may be purified according to customary methods, for example by recrystallization, or if spray dried the resulting complex may be directly employed for preparation of galenical forms.

Magnesium monospartate hydrochloride is a colorless crystalline substance (transparent plates and prisms), which in the form of an 1% aqueous solution has a pH of about 7 and a 6% 1N HCl solution has a specific rotation of +12.5 ± 2. The mixed melting point of this compound with dicyanodiamide is 188° C. Solubility in water amounts to 1:5 (cold), while the compound is difficultly soluble in alcohol, acetone and chloroform.

In the preparation of magnesium monospartate hydrochloride, hydrochloric acid must be quickly added to the solution of magnesium diaspartate.

The magnesium hydrochloride complex employed in the present invention has an unexpectedly high complex stability. The magnesium glutamate hydrohalide analogues on the other hand have a considerably lower complex stability. The high complex stability of the complex employed in the present invention is highly advantageous for a series of reasons. Particularly, the monospartate hydrochloride portion of the magnesium complex apparently acts as an excellent carrier for magnesium. This is particularly significant in the case of magnesium monospartate hydrochloride.

The magnesium monospartate hydrochloride complex has, contrary to earlier indications, surprisingly been found to be useful in the prophylaxis of metabolic heart necroses. Particularly significant is that the complex also exhibits the prophylactic activity when administered orally. However, dosages may be administered both enterrally or parenterally. Enteral daily dosages at which satisfactory results are obtained range from about 4 mg/kg to about 50 mg/kg animal body weight and the daily oral dosage indicated for practical use in larger mammals ranges from about 300 to about 7000 mg/day. Parenteral dosage is also possible, and such daily dosages should not exceed about 50 mg/kg/day animal body weight, and the daily parenteral dosage in larger mammals ranges from about 300 to about 3000 mg/day. The dosage forms suitable for oral administration include tablets, dragees, capsules, syrups and solutions. The active agent may be mixed with conventional inert pharmaceutical carriers or diluents.

The prophylactic activity of magnesium monospartate hydrochloride is particularly surprising in that a series of works on the analogous magnesium aspartate did not show any therapeutic effect on the occurence of metabolic heart necroses.

An example of a galenical form suitable for oral administration and comprising the magnesium monospartate hydrochloride complex, corresponding to a magnesium content of 121.56 mg is described below. The carriers are exemplary.

EXAMPLE 1

| | |
|---|---:|
| Magnesium monoaspartate hydrochloride complex | 1.242,9 mg |
| Thiamine hydrochloride | 2,0 mg |
| Riboflavine | 3,0 mg |
| Pyridoxine hydrochloride | 3,0 mg |
| Sugar | 3.219,1 mg |
| Sacharine 75% | 10,0 mg |
| "Mandarinenaroma Polyrome 3549" | 20,0 mg |
| Citric acid | 500,0 mg |
| | 5.000,0 mg |

The magnesium complex employed in the present invention is very satisfactorily resorbed, as indicated by resorption tests carried out on test animals.

The magnesium monospartate hydrochloride complex can also be prepared according to the process of the German Offenlegungsschrift No. 2,228,101 by reacting equimolecular amounts of magnesium-L-diaspartate with magnesium chloride in aqueous solution and converting the obtained complex into the solid form by spray-drying.

The following example 2 illustrates this process.

EXAMPLE 2

Preparation of a magnesium-L-aspartic acid chlorine complex, 1 Mg . 1 (aspartic acid — 2H) . 1 Cl.

To a solution of 133.43 g (0.4 mol) of magnesium-L-diaspartate ($Mg(Asp)_2 \times 2.5H_2O$; mol.wt. 333.55) in 500 ml of water (40° C.) add while stirring, a solution of 81.34 g (0.4 mol) of magnesium chloride ($MgCl_2 . 6H_2O$; mol.wt. 203.32) in 100 ml of water (40° C.). The complex is obtained directly from the resulting solution by means of spray drying at 160° to 180° C. A white powder containing about 4 to 5 percent of water is obtained.

The complex exhibits a significant jump in temperature at 210° C. (beginning disintegration) (temperature gradient: 40° C. per min.), which differs clearly from that of magnesium diaspartate, which shows a minimal jump at 194° C. and which is stable up to a temperature in excess of 300° C.

What is claimed is:

1. A method of treating heart necroses comprising administering orally, enterally or parenterally to a patient in need of said treatment a heart necrosis inhibiting amount of magnesium monospartate hydrochloride complex.

2. A method according to claim 1, in which the magnesium monospartate hydrochloride complex is administered in association with an inert pharmaceutical carrier or diluent.

3. A method according to claim 2, in which the magnesium monospartate hydrochloride complex is administered enterally, at daily dosage of from 4 mg/kg to 50 mg/kg animal body weight.

4. A method according to claim 3, in which the magnesium monospartate hydrochloride complex is administered at a daily dosage of from 300 to 7000 mg.

5. A method according to claim 2, in which the magnesium monospartate hydrochloride complex is administered parenterally, at a daily dosage not exceeding 50 mg/kg animal body weight.

6. A method according to claim 5, in which the magnesium monospartate hydrochloride complex is administered at a daily dosage of from 300 to 3000 mg.

* * * * *